(12) United States Patent
Reimink et al.

(10) Patent No.: US 7,604,663 B1
(45) Date of Patent: Oct. 20, 2009

(54) MEDICAL DEVICES WITH POLYMER/INORGANIC SUBSTRATE COMPOSITES

(75) Inventors: Matthew S. Reimink, New Brighton, MN (US); Matthew F. Ogle, St. Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 694 days.

(21) Appl. No.: 09/475,721

(22) Filed: Dec. 30, 1999

(51) Int. Cl.
*A61F 2/24* (2006.01)

(52) U.S. Cl. .................................. 623/2.1; 623/1.1

(58) Field of Classification Search ....... 623/1.11–2.42; 428/548, 615, 625
See application file for complete search history.

(56) References Cited

U.S. PATENT DOCUMENTS

| | | | | |
|---|---|---|---|---|
| 3,579,645 A | | 5/1971 | Bokros | 3/1 |
| 3,722,004 A | * | 3/1973 | Cromie | 3/1 |
| 4,263,680 A | * | 4/1981 | Reul et al. | 3/1.5 |
| 4,265,694 A | * | 5/1981 | Boretos et al. | 156/242 |
| 4,312,920 A | * | 1/1982 | Pierce et al. | 428/425.5 |
| 4,597,767 A | * | 7/1986 | Lenkei | 623/2.22 |
| 4,627,836 A | * | 12/1986 | MacGregor | 604/93 |
| 4,776,337 A | * | 10/1988 | Palmaz | 623/1.11 |
| 4,778,461 A | * | 10/1988 | Pietsch et al. | 623/2 |
| 4,822,355 A | | 4/1989 | Bhuvaneshwar | 623/2 |
| 4,888,009 A | * | 12/1989 | Lederman et al. | 623/2.19 |
| 5,073,171 A | | 12/1991 | Eaton | 604/266 |
| 5,089,020 A | * | 2/1992 | Koppert | 623/3.21 |
| 5,304,121 A | | 4/1994 | Sahatjian | 604/53 |
| 5,380,299 A | | 1/1995 | Fearnot et al. | 604/265 |
| 5,383,928 A | * | 1/1995 | Scott et al. | 623/1.12 |
| 5,413,599 A | * | 5/1995 | Imachi et al. | 623/2 |
| 5,464,650 A | | 11/1995 | Berg et al. | 427/2.3 |
| 5,500,016 A | * | 3/1996 | Fisher | 623/2.19 |
| 5,522,882 A | * | 6/1996 | Gaterud et al. | 623/1.11 |
| 5,545,208 A | | 8/1996 | Wolff et al. | 623/1 |
| 5,562,729 A | * | 10/1996 | Purdy et al. | 623/2 |
| 5,578,075 A | | 11/1996 | Dayton | 623/1 |
| 5,591,227 A | | 1/1997 | Dinh et al. | 623/1 |

(Continued)

FOREIGN PATENT DOCUMENTS

WO    WO 98/36784    8/1998

(Continued)

OTHER PUBLICATIONS

Sumitomo Electric Ind, Co, Oct. 1984, Abstract JP 59192366A.*

(Continued)

*Primary Examiner*—David R Sample
*Assistant Examiner*—S. Hon
(74) *Attorney, Agent, or Firm*—Westman, Champlin & Kelly, P.A.; Hallie A. Finucane

(57) ABSTRACT

Improved medical device have an inorganic substrate and a polymer covering at least a portion of the substrate, in which the polymer forms a structure substantially different from the structure of the substrate. Other medical devices include a flexible composite component with an inorganic substrate and a polymer covering at least over a portion of the substrate. The flexible composite component can be bent, at least, about 100 degrees without extending the material beyond its elastic limit. Corresponding methods include applying a polymer onto an inorganic substrate, such that the polymer does not conform to the shape of the substrate.

11 Claims, 3 Drawing Sheets

U.S. PATENT DOCUMENTS

| | | | |
|---|---|---|---|
| 5,609,631 A | 3/1997 | Rubens et al. | 623/11 |
| 5,693,085 A | 12/1997 | Buirge et al. | 623/1 |
| 5,693,098 A | 12/1997 | Rubens et al. | 623/11 |
| 5,735,892 A * | 4/1998 | Myers et al. | 623/1.13 |
| 5,738,902 A | 4/1998 | Forrestal et al. | 427/2.12 |
| 5,765,682 A * | 6/1998 | Bley et al. | 206/363 |
| 5,788,979 A | 8/1998 | Alt et al. | 424/426 |
| 5,804,263 A | 9/1998 | Goldberg et al. | 428/34.7 |
| 5,824,048 A | 10/1998 | Tuch | 623/1 |
| 5,824,054 A * | 10/1998 | Khosravi et al. | 623/1.44 |
| 5,837,313 A | 11/1998 | Ding et al. | 427/2.21 |
| 5,866,113 A | 2/1999 | Hendriks et al. | 424/78.17 |
| 5,868,780 A * | 2/1999 | Lashinski et al. | 606/198 |
| 5,891,196 A | 4/1999 | Lee et al. | 8/94.11 |
| 5,891,506 A | 4/1999 | Keogh | 427/2.13 |
| 5,891,507 A | 4/1999 | Jayaraman | 427/2.25 |
| 5,897,911 A | 4/1999 | Loeffler | 427/2.25 |
| 5,910,170 A * | 6/1999 | Reimink et al. | 623/2.38 |
| 5,922,393 A | 7/1999 | Jayaraman | 427/2.3 |
| 5,947,925 A * | 9/1999 | Ashiya et al. | 604/164.08 |
| 6,139,575 A | 10/2000 | Shu et al. | |
| 6,322,588 B1 * | 11/2001 | Ogle et al. | 623/1.46 |
| 6,808,533 B1 * | 10/2004 | Goodwin et al. | 623/1.13 |

FOREIGN PATENT DOCUMENTS

| | | |
|---|---|---|
| WO | WO 99/57581 | 11/1999 |
| WO | WO 00/32255 | 6/2000 |

OTHER PUBLICATIONS

Sumitomo Electric Ind, Co, May 1984, Abstract JP 59082851A.*
Mark Alger, "Polymer Science Dictionary", $2^{nd}$ Edition, 1997, pp. 521-522.*
International Search Report dated Jun. 12, 2001 for International Application No. PCT/US00/35122.

* cited by examiner

MEDICAL DEVICES WITH POLYMER/INORGANIC SUBSTRATE COMPOSITES

BACKGROUND OF THE INVENTION

The invention relates to medical devices suitable for contacting a patient's bodily fluids, including a substrate with a polymer material covering at least a portion of the substrate.

A variety of medical devices are designed particularly for contact with a patient's bodily fluids. The duration of this contact may be relatively short, as is typical with surgical instruments, or may be long term, as is typical with prosthetic heart valves implanted into the body of a recipient, and other implanted prostheses. Some articles such as catheters can have either short term or relatively long term contact.

Prostheses, i.e., prosthetic articles, are used to repair or replace damaged or diseased organs, tissues and other structures in humans and animals. Prostheses generally must be biocompatible since they are typically implanted for extended periods of time. Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the native valve and surgical replacement with a mechanical or bioprosthetic, i.e., tissue based, valve. Another technique uses an annuloplasty ring to provide structural support to the natural annulus of the native valve.

Many biocompatible medical devices and/or their components have specific requirements with respect to their mechanical and physical properties. For example, the medical devices are often limited in their size while needing fairly complex structural features. At the same time, the devices and/or their components may be subjected to demanding mechanical requirements, such as mechanical strength and long term wear requirements. Thus, there are significant restraints imposed on the design of many medical devices and/or their components.

As a particular example, heart valve stents are used to support leaflet components within a bioprosthetic heart valve. Heart valve stents have been produced from polymers, such as polyacetals, for example Delrin® and Celcon®, or metals, such as titanium or a cobalt-chromium-nickel alloy, for example, Elgiloy® Polymer heart valve stents have been known to fail due to fatigue and creep. Furthermore, polymer heart valve stents need to be relatively bulky in order to withstand the repeated loading over the lifetime of the prosthetic valve.

In contrast, heart valve stents made from spring metals, such as Elgiloy®, exhibit better mechanical properties, such as strength and fatigue endurance, and can have a smaller cross-section than corresponding polymer stents. Metal heart valve stents, however, generally must be kept quite simple in geometry, and typically consist of a simple wire form. As the geometry of the metal stent becomes more complex, the stent generally includes more metal joints, which can weaken the structure. Also, metal stents may require welding or crimping during their manufacture which can weaken the stent. Similar observations regarding properties and construction of heart valve stents can also apply to other medical devices and their components.

SUMMARY OF THE INVENTION

In a first aspect, the invention pertains to a medical device comprising an inorganic substrate and a polymer covering at least a portion of the substrate. The polymer forms a structure substantially different from the structure of the substrate.

In another aspect, the invention pertains to a medical device comprising a flexible composite component. The flexible composite component includes an inorganic substrate and a polymer covering at least over a portion of the substrate. The flexible composite component can be bent, at least, about 10 degrees without extending the material beyond its elastic limit.

In a further aspect, the invention pertains to a method of forming a medical device, the method including applying a polymer onto an inorganic substrate. The polymer is applied over the substrate such that the polymer does not conform to the shape of the substrate.

DETAILED DESCRIPTION OF THE ILLUSTRATIVE EMBODIMENTS

Figure 1:
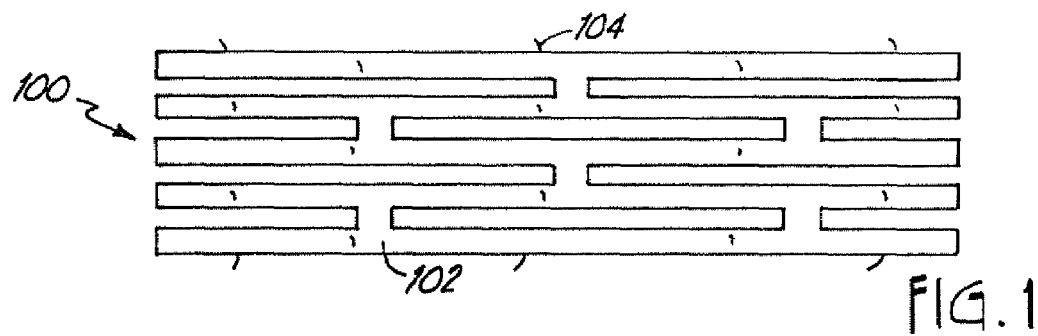
FIG. 1 is a side view of a vascular stent.

Biocompatible medical devices can be formed from a composite having an inorganic substrate, which imparts desired mechanical properties, and a polymer member, which provides appropriate flexibility and/or geometric features. The polymer member of the composite covers at least a portion of the inorganic substrate. In particular, the mechanical properties of the polymer/substrate composite can be adjusted by selecting the compositions and/or dimensions to yield acceptable levels of durability and desired amounts of flexibility or rigidity. The polymer member provides the form or geometry for the ultimate medical device or component. Polymers can be applied over a substrate to form complex geometries that may be desirable or required for the function of the medical device or component. For flexible components, the polymers can contribute to the flexibility of the component along with the substrate.

A variety of medical articles can be used to contact bodily fluids of a patient. Relevant biocompatible medical articles generally incorporate a biocompatible material which is intended to contact the patient's biological fluids and/or tissues. Bodily fluids include, for example, blood, plasma, serum, interstitial fluids, saliva and urine. The patient can be an animal, especially a mammal, and preferably is a human.

Relevant medical articles include devices that contact a person's bodily fluids for varying lengths of time, for example, prostheses, catheters and surgical instruments. Prostheses, i.e., prosthetic articles, are used to repair or replace damaged or diseased organs, tissues and other structures in humans and animals. Prostheses generally must be biocompatible since they are typically implanted for extended periods of time. Relevant prostheses include prostheses used in the cardiovascular system in which size constraints impose significant performance requirements on the materials without sacrificing the biocompatibility and durability of the prostheses.

The inorganic substrate for the substrate/polymer composite can be formed, for example, from metals, ceramics, carbon based solids or combinations thereof. The substrate can be formed as a unitary piece, or it can have layers or other discernable structure. The substrate may be formed to have the general size and shape of the final device or component, such that the substrate can contribute significantly to the overall mechanical properties of the composite.

Generally, the substrate is relatively simple with respect to structural features. It can be relatively difficult and/or costly to introduce more complex features into substrates formed with the inorganic materials. The substrates, however, can contribute significantly to obtaining desired levels of mechanical strength, fracture toughness, fatigue resistance, wear/tear resistance, resiliency and other desirable mechanical properties without adding excessive bulk and weight.

The polymer member can cover all or a portion of the inorganic substrate. If the inorganic substrate is completely covered with polymer, the substrate generally does not have to be biocompatible. Many polymers are biocompatible, in that they are non-toxic, non-carcinogenic and do not induce hemolysis or a significant immunological response. Blood contacting medical devices formed from polymers should be non-thrombogenic.

Polymers are an appealing biocompatible material for use in medical devices that contact bodily fluids since polymer components can incorporate complex structural features and a desirable range of mechanical properties. Polymers can be selected to have desired amounts of stiffness or flexibility as well as durability and hardness. While polymers can have desirable mechanical properties, such as strength, fatigue resistance and wear/tear resistance, polymer components having desirable levels of these properties may have excessive polymer bulk. Use of an inorganic substrate with a polymer member can reduce the overall bulk of the composite while obtaining the desired mechanical properties. The polymer member can be formed with a relatively complex geometry that is not reflected in the structure of the substrate.

Furthermore, polymers can be formed into components with a variety of shapes and sizes. For example, flexible polymers can be used to form components, such as flexible valve occluders/leaflets of valved grafts or conduits, vascular stents, heart valve stents, valved vein grafts or heart valve prostheses. The composites described herein are particularly suited to the formation of flexible medical devices or flexible components since the polymers can supply desired levels of flexibility while the substrate can improve strength and durability without sacrificing flexibility or contributing excessively to the composite bulk. In addition, rigid polymers can be used, for example, to form rigid occluders/leaflets in mechanical heart valve prostheses.

Medical Devices

Relevant biocompatible articles include all medical devices that contact bodily fluids and/or tissue. These articles can be organized roughly into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a moist membrane, such as within a patient's mouth.

Implanted devices and components thereof include, without limitation, prostheses such as pacemakers, electrical leads such as pacing leads, defibrillators, artificial organs such as artificial hearts, ventricular assist devices, anatomical reconstruction prostheses such as jaw implants, artificial heart valves, heart valve stents, valve leaflets, orifice rings of mechanical heart valves, pericardial patches, surgical patches, coronary stents, vascular grafts, vascular, cardiovascular and structural stents, vascular and cardiovascular shunts, biological conduits, pledgets, suture, annuloplasty rings, stents, staples, connectors, valved grafts, dermal grafts for wound healing, orthopedic and spinal implants, orthopedic pins, intrauterine devices (IUDs), urinary stents, permanently indwelling pericardial devices, maxial facial reconstruction plating, dental implants, intraocular lenses, clips, sternal wires, bone prostheses, skin prostheses, ligament prostheses, tendon prostheses, and combinations thereof.

Percutaneous devices include, without limitation, angioplasty balloons, catheters of various types, cannulas, drainage tubes such as chest tubes, surgical instruments such as forceps, retractors, needles, and gloves, and catheter cuffs. Catheters can be used for accessing various bodily systems such as the vascular system, the gastrointestinal tract, or the urinary system.

Cutaneous devices include, without limitation, burn dressings, wound dressings and dental hardware, such as bridge supports and bracing components. These biocompatible articles can be made from the biocompatible materials described below.

While the polymer/inorganic substrate composites can be used in any of the medical devices described above, a few medical devices are of particular interest. Such devices of particular interest include, for example, heart valve prostheses, heart valve stents, heart valve leaflets, vascular stents, urinary stents, annuloplasty rings, mechanical heart valve components, pacemaker components, catheters, electrical leads, left ventricular assist devices, and orthopedic components.

Figure 2:
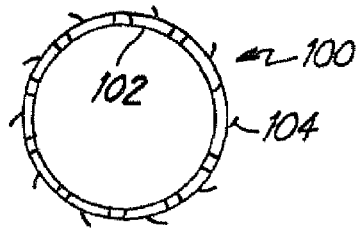
FIG. 2 is an end view of the vascular stent of FIG. 1.

Particularly preferred medical devices or device components include, for example, annuloplasty rings, vascular stents, heart valve leaflets and heart valve stents. A representative vascular stent design is shown in FIGS. 1 and 2. Vascular stent 100 is formed from a biocompatible material 102 with a form consistent with its expandable nature, as described further below. Polymer anchors 104 extend outward from vascular stent 100. When vascular stent 100 is deployed, polymer anchors 104 grip tissue and/or plaque in the wall of the blood vessel to help secure the stent.

Figure 3:
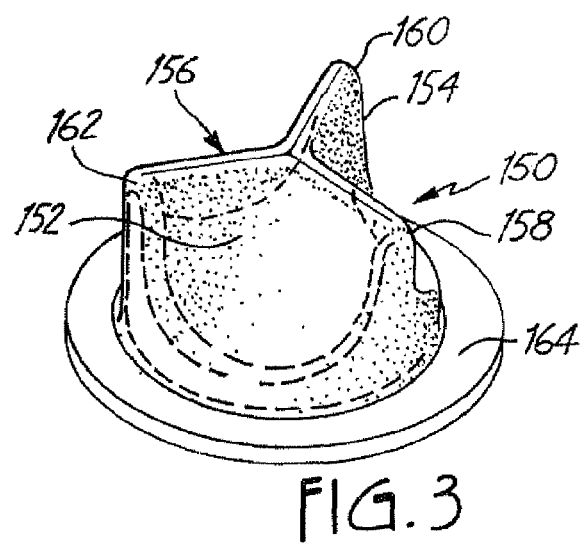
FIG. 3 is a perspective view of a heart valve prosthesis having flexible composite leaflets.
Figure 4:
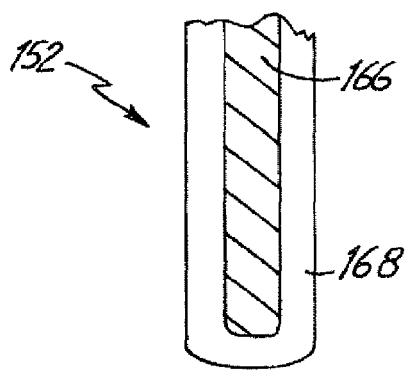
FIG. 4 is a fragmentary, schematic view of a cross section of a composite leaflet.

An embodiment of a heart valve prosthesis with flexible composite leaflets or occluders is shown in FIG. 3. Heart valve prosthesis 150 includes leaflets 152, 154, 156 joined at commissures 158, 160, 162, and sewing ring 164. Sewing ring 164 is used to attach valve 150 to patient tissue with sutures, adhesives or other attachment mechanisms. A partial cross section of leaflet 152 is shown in FIG. 4, in which a flexible inorganic substrate 166 is covered with a polymer member 168. While the heart valve prosthesis in FIGS. 3 and 4 is shown with three polymer leaflets, prostheses can be constructed with different numbers of polymer leaflets, such as two leaflets.

A flexible composite used to form the leaflets of heart valve prosthesis 150 preferably has sufficient durability to withstand the repeated cycling required for replacement heart valve use. The valve must cycle about 40 million times each year, and the valve ideally must remain functional over the remaining natural expected lifetime of the patient. Depending on the age of the patient at implantation, this natural lifetime may range from about 10 years in an elderly patient to about 60 years to even about 100 years in a young patient. Current tissue valves may require replacement following about 400 million to about 600 million cycles. Therefore, the composite leaflet preferably can withstand at least about 400 million cycles and more preferably can withstand more than about 600 million cycles without significant structural failure. Flexible heart valve leaflets generally flex from about 20° to about 90° in each cycle and more typically flex from about 40° to about 70° in each cycle. While the leaflets generally flex within this range during their cycling, the leaflets preferably can be flexed about 180° multiple times without extending the material beyond its elastic limit.

Figure 5A:
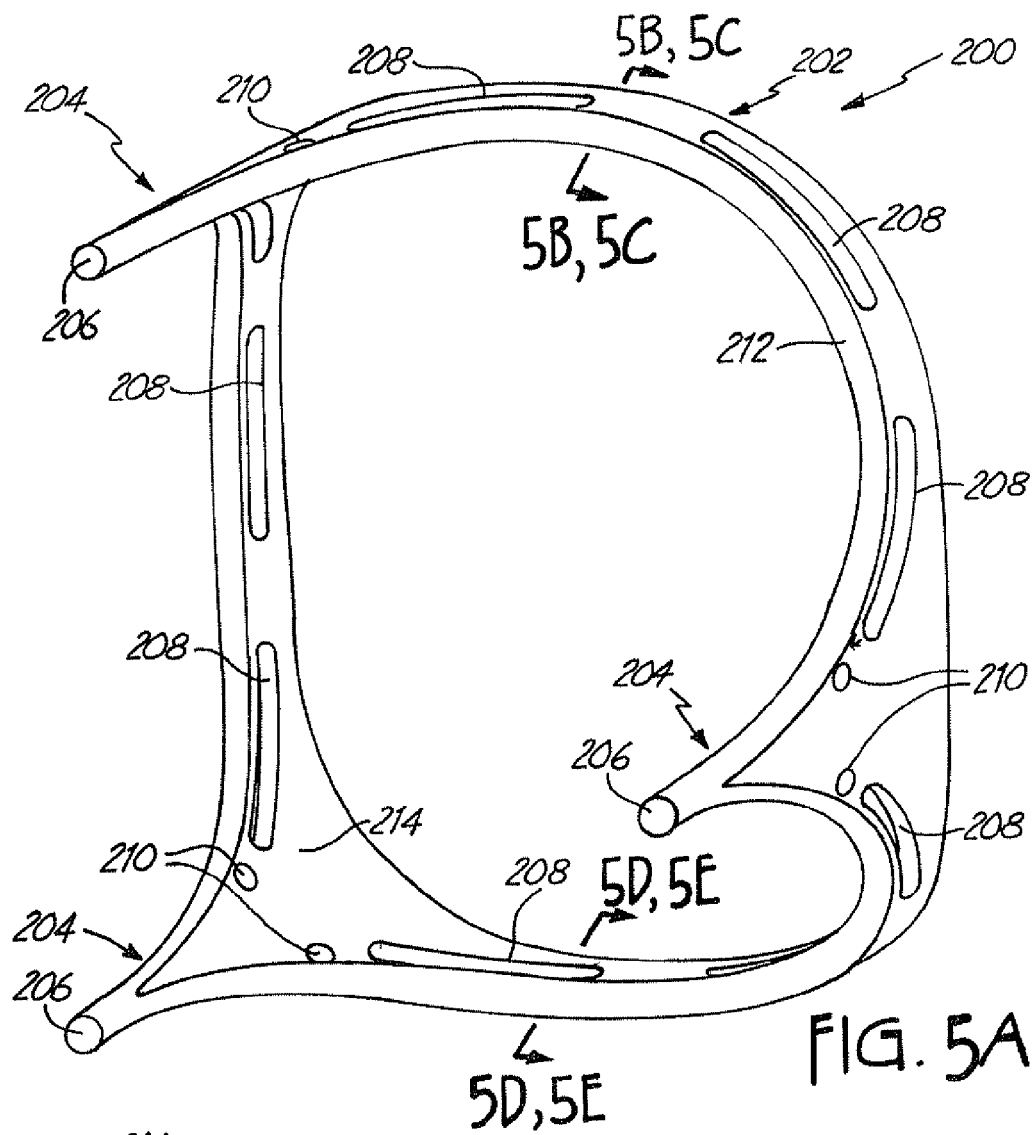
FIG. 5A is a perspective view of a heart valve stent for supporting leaflets of a heart valve prosthesis.

A first embodiment of a heart valve stent 200 is shown in FIG. 5A. Heart valve stent 200 includes an inflow ring 202, which may be scalloped, and commissure posts 204, which extend to individual post tips 206. Inflow ring 202 has a generally annular configuration. Stent 200 includes openings 208 and retaining holes 210, either or both of which can be used to couple biocompatible material to the stent. Stent 200 includes a ridge 212 that extends along the top of stent 200 with sharper bends at post tips 206. Flexible support 214 extends from ridge 212 to form inflow ring 202. In some embodiments, ridge 212 is thicker than flexible support 214. Stent 200 provides a suitable surface for supporting cusps or leaflets of biocompatible material and other components of a heart valve prosthesis.

Preferably, stent 200 has a flexibility approximating the native supporting structure of the patient's tissue. The flexibility of stent 200 can be different at different points along stent 200. Generally, ridge 212 is more rigid than flexible support 214. Preferably, heart valve stent 200 is formed from the polymer/inorganic substrate composites described herein. An inorganic substrate can be located within ridge 212 and/or flexible support 214.

Figure 5B:
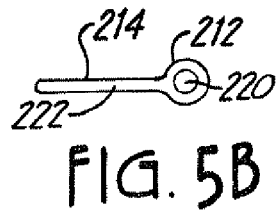
FIG. 5B is a sectional view of the heart valve stent of FIG. 5A taken along line BC-BC of FIG. 5A.
Figure 5C:
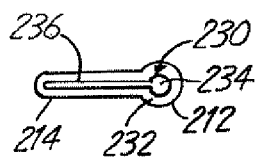
FIG. 5C is a sectional view of an alternative embodiment of the heart valve stent of FIG. 5A taken along line BC-BC of FIG. 5A.
Figure 5D:
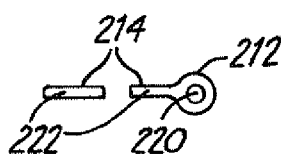
FIG. 5D is a sectional view of the heart valve stent of FIG. 5A taken along line DE-DE of FIG. 5A.
Figure 5E:
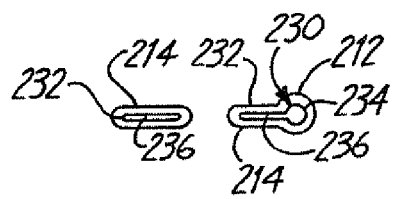
FIG. 5E is a sectional view of the alternative

An embodiment with an inorganic substrate just within a thickened ridge 212 is depicted in the cross sections of FIGS. 5B and 5D. Substrate 220 extends through all or a portion of ridge 212, and polymer 222 covers substrate 220 as well as forming flexible support 214. An alternative embodiment is shown in the cross sections of FIGS. 5C and 5E. In this alternative embodiment, substrate 230 extends through the entire cross section of stent 200, and polymer 232 covers the entire substrate 230. Inorganic substrate 230 includes a ridge portion 234 and a thinner extension portion 236. Ridge portion 234 and extension portion 236 can be formed from the same material or a different material. In one preferred embodiment, ridge portion 234 is formed from a more rigid metal, such as titanium, and extension portion 236 can be formed from a more flexible metal, such as a spring metal. Suitable spring metals include, for example, Elgiloy® and other cobalt alloys.

Figure 6:
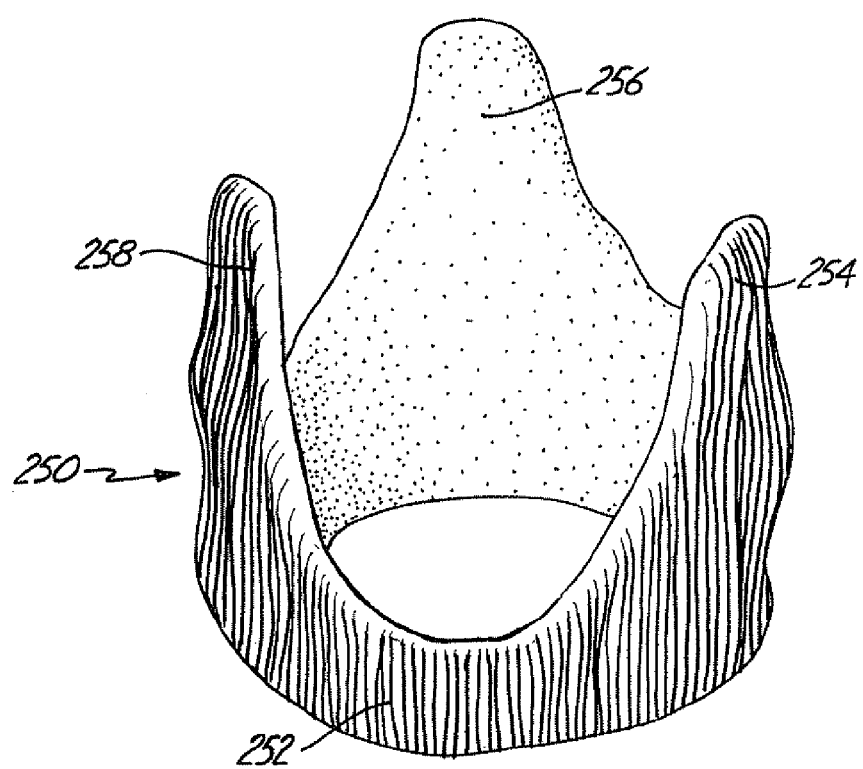
FIG. 6 is a perspective view of a sheath-type heart valve stent for supporting leaflets of a heart valve prosthesis.

An alternative embodiment of a heart valve stent 250 is depicted in FIG. 6. Sheath shaped heart valve stent 250 has a generally annular base 252 and three commissure supports 254, 256, 258 extending upward from base 252 at roughly equal spacings around the circumference of base 252. As with heart valve stent 200, heart valve stent 250 preferably has a flexibility approximating the native supporting structure of the patient's tissue. The flexibility of heart valve stent 250 can be different at different points along stent 250 to more closely match the flexibility of the native supporting structure. Leaflets and other components of a heart valve prosthesis can be attached to heart valve stent 250 with suture or other appropriate method. Heart valve stents 200 and 250, respectively should be strong enough to withstand the closing forces subjected on the valve.

Biocompatible Materials

The medical devices of interest include at least a component comprising the polymer/inorganic substrate composites described herein. The portions of the medical devices that are designed to contact the bodily fluids or tissues of a patient can include additional biocompatible materials, such as tissue, polymers not associated with an inorganic substrate, metal, and ceramics, within the same component as the polymer/inorganic substrate composite or in separate components. These optional additional biocompatible materials are described in this section.

Appropriate biocompatible materials can be formed from natural materials, synthetic materials or combinations thereof. These tissues may be obtained from, for example, native heart valves, portions of native heart valves such as aortic roots, walls and leaflets, pericardial tissues, such as pericardial patches, connective tissues, bypass grafts, tendons, ligaments, skin patches, blood vessels, cartilage, dura mater, skin, bone, fascia, submucosa, umbilical tissues, and the like. Natural, i.e., biological, material for use in the invention includes relatively intact living tissue, decellularized tissue and recellularized tissue.

Natural tissues are derived from a selected animal species, typically mammalian, such as human, bovine, porcine, seal, equine, canine or kangaroo. These natural tissues generally include collagen-containing material. Natural tissue is typically, but not necessarily, soft tissue. Tissue materials are particularly useful for the formation of tissue heart valve prostheses.

Tissues can be fixed by crosslinking. Fixation provides mechanical stabilization, for example, by preventing enzymatic degradation of the tissue. Glutaraldehyde or formaldehyde is typically used for fixation, but other fixatives can be used, such as other polyfunctional aldehydes, epoxides, and genipin and derivatives thereof. Tissues can be used in either crosslinked or uncrosslinked form, depending on the type of tissue, the use and other factors. Generally, if xenograft tissue is used, the tissue is crosslinked and/or decellularized.

Relevant synthetic materials include, for example, polymers and ceramics. Appropriate ceramics include, without limitation, hydroxyapatite, alumina and pyrolytic carbon. Appropriate synthetic materials include hydrogels and other synthetic materials that cannot withstand severe dehydration. Biocompatible materials can be fabricated from synthetic polymers as well as purified biological polymers. Suitable synthetic polymers are described below with respect to the formation of polymer members of the composites. These synthetic polymeric materials can be formed into fibers and then can be woven or knitted into a mesh to form a matrix or similar structure. Alternatively, the synthetic polymer materials can be molded or cast into appropriate forms.

Biological polymers can be naturally occurring or produced in vitro by fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Inorganic Substrates

The composites described herein have an inorganic substrate onto which a polymer member is applied. The inorganic substrates can be formed from metals, metal compounds, ceramics, carbon based solids, alloys thereof and combinations thereof. While the polymer can impart significant structural features to the composite, the substrate may provide the overall shape, size and/or strength of the resulting composite. The inorganic substrate typically is formed from biocompatible materials, although the substrate does not need to be biocompatible if the substrate is completely covered by polymer.

Suitable metals for use within the inorganic substrate include, for example, titanium, cobalt, stainless steel, nickel, iron alloys, cobalt alloys, such as Elgiloy®, a cobalt-chromium-nickel alloy, and MP35N, a nickel-cobalt-chromium-molybdenum alloy, and Nitinol®, a nickel-titanium alloy. Suitable metals also include metals doped with small amounts of other elements, such as steel, i.e., iron doped with a small amount of carbon. To form flexible elements, spring metals, such as Elgiloy® can be used. Suitable metal compounds include, for example, compounds insoluble in water, such as metal oxides, metal carbides and metal nitrides, which generally are rigid, hard materials.

Suitable ceramics (some of which are also metal compounds) include, for example, hydroxyapatite, alumina, silicon oxide, silicon carbide, silicon nitride, boron carbide and boron nitride. Suitable carbon-based solids include, for example, diamond, graphite, amorphous carbon, diamond-like carbon, pyrolytic carbon and pyrolytic graphite. Carbon-based solids are considered inorganic materials, as used herein, as long as the local structure of the material is dominated by a carbon-carbon solid structure even if the material contains small to moderate amounts of non-carbon elements. For example, pyrolytic carbon can contain some hydrogen, oxygen and/or nitrogen without losing $sp^2$ carbon-carbon graphitic bonding that dominates the structure, and diamond-like carbon can similarly include some hydrogen, nitrogen and oxygen without losing $sp^3$ carbon-carbon diamond bonding that dominates the structure.

The inorganic substrate can be itself a composite material with layers. For example, the substrate can have a graphite core with pyrolytic carbon deposited on top of the graphite. Similarly, the substrate can include a plurality of materials that are joined or welded to form the substrate. In this way, different portions of the substrate can have different mechanical properties desired for that portion of the substrate.

As noted above, the substrate may or may not have the overall shape and approximate size of the subsequent medical article or component. Regardless, the composite may have a volume percent of the substrate less than about 50 percent, and possibly less than about 25 percent. For example, a flexible component can include a thin metal foil or the like as the substrate with a flexible polymer material, in which the substrate forms less than a majority of the volume of the composite. In alternative embodiments, the substrate can occupy a large volume fraction of the composite, in which the polymer member forms a relatively thin covering relative to the overall thickness of the composite. In some embodiments, the composite can include a substrate that occupies greater than about 80 volume percent of the composite. In addition, the polymer member can form additional structural features that extend from the composite without being defined by the underlying substrate, as described further below.

Generally, the inorganic substrate has a thickness greater than about 10 microns. For rigid components, the inorganic substrate preferably has a thickness at least about 100 microns, not greater than about 500 microns, and more preferably from about 250 microns to about 500 microns. For flexible components, the inorganic substrate generally has a thickness from about 10 microns to about 500 microns and preferably from about 50 microns to about 200 microns.

The approaches used to produce the substrate generally depend on the composition of the substrate. Suitable methods include conventional methods that can be employed to produce the element if the substrate were not going to be covered subsequently with polymer. In other words, metal components can be produced with conventional methods used to produce metal components for medical device, and similarly for the other materials. Suitable methods generally include machining, molding, casting, shaping, sputtering, laser machining, electrical discharge machining, welding and the like.

Polymer Members

To form the composite materials, a polymer composition is applied over at least a portion of the surface of an inorganic substrate. The particular polymer is selected to yield the desired mechanical properties with respect to, for example, durability, mechanical strength, and flexibility/rigidity. In addition, the polymer can be used to add structural features that may be difficult to add directly into the structure of the inorganic substrate. The polymer should also be inert with respect to compounds in a patient's bodily fluids and tissues.

Polymeric materials can be fabricated from synthetic polymers as well as purified biological polymers. Appropriate synthetic polymers may include hydrogels and other synthetic polymers that cannot withstand severe dehydration. Construction of the prosthesis can be completed following deposition of appropriate polymer members since additional components of the final prosthesis may interfere with the deposition of the polymer. However, in some embodiments, the polymer can be applied to a component with an inorganic substrate by appropriate methods following assembly with additional components if the additional components do not block relevant surfaces of the inorganic substrates.

Appropriate synthetic polymers include, without limitation, polyamides (e.g., nylon) polyesters, polystyrenes, polyacrylates, vinyl polymers (e.g., polyethylene, polytetrafluoroethylene or other halogenated polymers such as polyvinylchloride, polypropylene, other polyolefins, ethylene-propylene copolymers, and ethylene-propylene-diene monomer copolymer (EPDM)), polycarbonates, polyacetals (e.g., Delrin®), polyurethanes, polydimethyl siloxanes, cellulose acetates, polymethylmethacrylates, ethylene vinyl acetates, polysulfones, nitrocelluloses, polyetheretherketones (PEEK) and copolymers and mixtures thereof. Biological polymers can be naturally occurring or produced in vitro by, for example, fermentation and the like. Suitable biological polymers include, without limitation, collagen, elastin, silk, keratin, gelatin, polyamino acids, polysaccharides (e.g., cellulose and starch) and copolymers thereof.

Preferred polymers are biocompatible. Based on desirable properties and experience in the medical device field, preferred polymers include, for example, polyetheretherketones, polyacetals, polyamides, polyurethanes, polytetrafluoroethylenes, polyester teraphthalates, polycarbonates, polysulfones, polypropylenes, and copolymers and mixtures thereof.

Flexible synthetic polymers are generally referred to as elastomers and rigid synthetic polymers are generally referred to as plastics. Polymers can be flexible or rigid depending on their composition and final form, including thickness. Flexible polymers include elastomers and other polymers that can sustain significant flexure, bending, twisting and/or deformation without structural failure. Particularly preferred flexible polymer materials for forming polymer members include, for example, polyurethanes, polydimethylsiloxanes and polytetrafluoroethylenes. Preferred rigid polymers for forming polymer members include, for example, polysulfones, polyacetals, polyethersulfones, polyarylsulfones, polyetheretherketones, and polyetherimides.

For preferred medical device embodiments, the polymer members generally have a thickness greater than about 10 microns. For flexible embodiments, the polymer members generally have a thickness from about 10 microns to about 600 microns and more preferably from about 50 microns to about 300 microns. For rigid embodiments of particular interest, the polymer members have a thickness less than about 2000 microns, preferably from about 100 microns to about 1200 microns and more preferably from about 200 microns to about 800 microns.

Some preferred flexible composites have moderate flexibility, such that the composite material can be bent at least about 10° without damage or loss of elasticity. In other preferred embodiments, the composites are very flexible. For preferred highly flexible composites, the polymer/inorganic substrate composite can be bent significantly, about 100° or more and preferably up to approximately 180° bending, without damage or loss of elasticity. In particular, at the specified level of bending, the composite is not extended beyond its elastic limit, at which point the material would not flex back to approximately its original position. Thus, the bent composite returns to its original form. In some highly flexible embodiments, it is desirable that the composite can be bent up to 180° with a radius of curvature comparable to or less than the thickness of the composite, without damage to the composite. As noted above, all flexible components for medical devices generally are expected to flex many millions of times over the lifetime of the medical device.

A variety of structural features for the medical article can be introduced into the polymer member with or without a structural basis from the inorganic substrate. Application of the polymer member tends to modify the details of the substrate, for example, by smoothing edges and filling the spaces. Furthermore, the polymer deposition process can be modified to introduce additional structure that does not result from simple application of a polymer material over the surface Appropriate processes are described further below. Suitable polymer structure for addition to the composite that does not result from the substrate include, for example, barbs, anchors, slots and/or holes for sutures and fasteners, such as pins and buttons, for attachment to a secondary assembly.

The polymer members can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. Other methods, for example, casting, extrusion, calendering, sputtering, solvent based processing procedures, such as spray coating and spin coating, and the like, may also be suitable to form the polymer members. For the formation of flexible composites, sputtering and spin coating are particularly preferred deposition methods.

Many processing methods are suitable for introducing structure, possibly complex structure, into the composite. In particular, molding methods can incorporate the desired structure into the mold, such that the structure is formed as part of the covering process. Alternatively, structure can be introduced as a separate step from the polymer deposition process. In particular, desired structure can be introduced by adding additional polymer of the same or different composition onto an initially formed polymer member or by removing a portion of polymer that is deposited in an initial covering process. The deposition of additional polymer in a subsequent step of the covering process can be performed by the methods described above, preferably with a molding process, a sputtering process or a spin coating process. Removal of deposited polymer to form structural features can be performed by mechanical abrasion, machining, laser cutting, chemical etching or radiation etching.

Surface Modifications of the Polymer Coverings

With the polymer/inorganic substrate composites described herein, the polymer can include surface modification to improve the performance of the material. For example, the polymer can be crosslinked at its surface or a thin coating of diamond-like carbon can be applied to the surface. Preferably, the surface modification of the polymer does not significantly change the mechanical properties of the composite. However, surface modification can be used to adjust appropriately the material properties such that the final composite has desired properties.

As noted above, the surface of the polymer can be crosslinked or cured to make the surface more inert to modification following contact with the patient's fluids and/or tissue. While crosslinking can make a polymer more rigid and brittle, the degree of crosslinking and the penetration depth of the crosslinking can be controlled to reduce the physical effects on the polymer characteristics. In some cases, a degree of desired property modification can be introduced by crosslinking. A variety of crosslinking approaches are available including, for example, chemical crosslinking, thermal or heat crosslinking, photochemical crosslinking, and radiation crosslinking.

In chemical crosslinking, the polymer is contacted with a polyfunctional compound that reacts with functional groups in the polymer. The degree of crosslinking and crosslinking penetration can be controlled by the concentration of crosslinking agent and the amount of time the composite contacts the crosslinking agent. For thermal based crosslinking, the polymer is heated to induce chemical crosslinking of the polymer based on thermal excitation of the crosslinking between functional groups of the polymer. Photochemical crosslinking is similar to chemical crosslinking except that light is needed to activate the functional groups of either the polymer or the crosslinking agent. In photochemical crosslinking, the degree of crosslinking can also be controlled with the light flux and illumination time.

Ionizing radiation can crosslink as well as degrade polymers. Suitable ionizating radiation for crosslinking include, for example, high energy photons, such as ultraviolet light or x-rays, plasmas, electrons, neutrons, protons or ion beams. The energy and flux of the radiation can be adjusted to obtain the desired degree of crosslinking without significantly modifying the properties of the polymer, unless modification is desired.

In addition, a further coating can be applied over the polymer. In particular, a diamond-like carbon coating can be applied to the surface of the polymer to make the surface very inert with respect to undesirable reactions with bodily fluids and resistant to calcification. Preferred approaches for applying the diamond-like carbon coating generally involve assisted deposition where the polymer material is mounted on a stage and ionic beams are used to form the coating at the surface from a precursor, such as organic compounds with a suitable boiling point, in particular polyphenylether. Preferred approaches include, for example, ion beam assisted deposition. Generally, the diamond-like carbon coatings are applied in a thickness from about 10 nm to about 10 microns (μm), and for flexible components preferably from about 100 nm to about 500 nm. Deposition of diamond-like carbon coatings onto polymers is described further in copending and commonly assigned U.S. patent application Ser. No. 09/437,167 to Woo et al., entitled "Medical Article With a Diamond-Like Carbon Coated Polymer," incorporated herein by reference.

Completion of the Medical Device, Storage, Packaging, Distribution and Use

The polymer/inorganic substrate composite can form an entire medical device itself, or the polymer/inorganic substrate composite can be incorporated with other biocompatible components into a medical device before or after formation of the polymer member. For example, a polymer/inorganic substrate composite forming a heart valve stent can be incorporated into a tissue heart valve prosthesis, prior to storage and/or distribution of the resulting prosthesis. While in principle the polymer deposition can be performed following the formation of a multiple component medical device, the polymer deposition to form a single component within the medical device generally would be performed prior to assembly of the components to avoid interference with the deposition process by the other components.

The polymer/inorganic substrate composite material can be stored appropriately prior to or following formation into a medical device. Generally, the composite would be stored in a dry, sterile environment. If materials in the medical device require moisture to maintain their integrity, such as tissue or hydrogel, the medical device with the metal/polymer composite can be stored in a moist, sterile environment. The moist environment can be maintained with or without immersing the medical device in a sterile liquid, such as aqueous glutaraldehyde. A suitable storage container to maintain a medical device without immersing the article is described in U.S. Pat. No. 5,960,956 to Langanki et al., entitled "Storage Container," incorporated herein by reference.

For distribution, the medical devices are placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling.

The containers are distributed to health care professionals for use in appropriate medical procedures, such as implantation of a prosthesis and the like.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A medical device comprising a flexible composite component comprising an inorganic substrate and a polymer member covering the substrate, wherein the flexible composite component can be bent through a cross section of the flexible component composite, and wherein the polymer member contacts bodily fluids and separates the bodily fluids from the substrate.

2. The medical device of claim 1 wherein the Inorganic substrate comprises a metal foil with a thickness less than about 500 microns.

3. The medical device of claim 1 wherein the polymer is selected from the group consisting of polyurethanes, polydimethylsiloxanes and polytetrafluoroethylenes.

4. The medical device of claim 1 wherein the polymer member has a thickness from about 10 microns to about 500 microns.

5. The medical device of claim 1 wherein the polymer member has a thickness from about 50 microns to about 300 microns.

6. The medical device of claim 1 wherein the medical device comprises a heart valve prosthesis and the composite component comprises leaflets.

7. The medical device of claim 1 wherein the flexible composite component can be bent about 180 degrees without extending the flexible composite component beyond its elastic limit.

8. The medical device of claim 1 wherein the flexible composite component can be bent about 180 degrees with a radius of curvature of about the thickness of the composite without extending the flexible composite component beyond its elastic limit.

9. The medical device of claim 1 wherein the flexible composite component can be bent about 60 degrees for about 40 million cycles without significant structural failure.

10. The medical device of claim 1 wherein the flexible composite component can be bent about 60 degrees for about 400 million cycles without significant structural failure.

11. The medical device of claim 1 further comprising a diamond-like carbon coating over at least a portion of the polymer member.

* * * * *